(12) United States Patent
Hesch

(10) Patent No.: US 6,500,814 B1
(45) Date of Patent: Dec. 31, 2002

(54) HORMONAL CONTRACEPTIVE

(75) Inventor: Rolf-Dieter Hesch, Constance (DE)

(73) Assignee: Wyeth Pharmaceuticals, St. Davids, PA (US)

( * ) Notice: Subject to any disclaimer, the term of this patent is extended or adjusted under 35 U.S.C. 154(b) by 0 days.

(21) Appl. No.: 09/508,648

(22) PCT Filed: Sep. 3, 1998

(86) PCT No.: PCT/DE98/02636

§ 371 (c)(1),
(2), (4) Date: Jun. 5, 2000

(87) PCT Pub. No.: WO99/12531

PCT Pub. Date: Mar. 18, 1999

(30) Foreign Application Priority Data

Sep. 11, 1997 (DE) .......................................... 197 39 916

(51) Int. Cl.[7] .............................................. A61K 31/56
(52) U.S. Cl. ........................ 514/170; 514/841; 514/843
(58) Field of Search ................................ 514/170, 841, 514/843

(56) References Cited

U.S. PATENT DOCUMENTS

| | | | | |
|---|---|---|---|---|
| 4,855,305 A | * | 8/1989 | Cohen | 514/171 |
| 5,418,228 A | * | 5/1995 | Bennink | 514/182 |
| 5,898,032 A | * | 4/1999 | Hodgen | 517/178 |
| RE36,247 E | | 7/1999 | Plunkett et al. | |

FOREIGN PATENT DOCUMENTS

| | | | |
|---|---|---|---|
| EP | 0309263 | * | 3/1989 |
| EP | 0309263 B1 | | 3/1989 |
| EP | 0 309 263 A1 | | 3/1989 |
| EP | 0628312 B1 | | 12/1994 |

OTHER PUBLICATIONS

Coutinho, E.M., et al. (1995) *Comparative Study on Intermittent Versus Continuous use of a Contraceptive Pill Administered by Vaginal Route*. Contraception 51(6):355–8.

Davies, Graham C., et al. (1992) *Ovarian Activity and Bleeding Patterns During Extended Continuous Use of a Combined Contraceptive Vaginal Ring*. Contraception 46(3):269–278.

Rizk, Diaa E.E., and Kumar, Rachana M., (1996) *Congential Afibrinogenemia: Treatment of excessive Menstrual Bleeding with Continuous Oral Contraceptive*. American J. Hematology 52(3):237–238.

* cited by examiner

Primary Examiner—Barbara P. Badio
(74) Attorney, Agent, or Firm—Knobbe, Martens, Olson & Bear, LLP

(57) ABSTRACT

The present invention relates to a hormonal contraceptive product having two hormonal components, an estrogen and a gestagen, and a process for the combined, continuous administration of the product of the invention.

3 Claims, No Drawings

HORMONAL CONTRACEPTIVE

This application is the U.S. National Phase under 35 U.S.C. §371 of International Application PCT/DE98/02636, filed Sep. 3, 1998, which claims priority of German application DE 19739916.9, filed Sep. 11, 1997.

The present invention relates to a hormonal contraceptive product with two hormonal components, the use thereof and a hormonal contraception process.

Since hormonal contraceptives became available in the 1960's, a number of hormonal components have been investigated with regards to their suitability in the most varied administration diagrams. A fundamental subdivision into combination and sequential products is possible.

For example, if the desired cycle time is 28 days, in the case of the known combination products administration takes place over 21 days in a constant or varying absolute and/or relative dosage of a combination of an estrogen product and a gestagen product, in which the estrogen product can e.g. be natural estrogen or synthetic ethinyl estradiol and the taking of the aforementioned 21 daily units is followed by a seven-day interval where there is a withdrawal bleeding simulating natural menstruation.

In the known sequential products, once again for a desired cycle time of 28 days, administration takes place for 7 days of a pure estrogen product and then for 15 days of a combination of an estrogen product and a gestagen product and here again there is then a taking-free period of e.g. 6 days when withdrawal bleeding occurs. It is admittedly already known to bridge the inherent taking intervals of combination and sequential products in the interest of greater taking security by administering within the days in question placebos. However, it has hitherto always been assumed that during the roughly one-week taking interval no hormones of the present type should be administered, in order to ensure a reliable withdrawal bleeding. Only in the case of substitution products in the menopause of older women have hormones been administered throughout the cycle, e.g. in the sequence 10 days estrogen product, 11 days combination of estrogen and gestagen product, 7 days estrogen product, 7 days estrogen product in a particularly low dosage, but said substitution products are unsuitable for ovulation inhibition.

The sequential products used in substitution therapy are in particular unsuitable for contraception because the natural estradiol does not prevent ovulation in the dosage administered and the phase in which gestagen is administered is too short, being only 11 days. However, in the case of the substitution products, the above-described sequential system guarantees a relatively good cycle control.

German patent 43 08 406 discloses a combination contraceptive product, which comprises one or more stages. At least one stage contains the combination of three components, namely a biogenous estrogen, a synthetic estrogen and a gestagen and the further stages in each case comprise a pharmaceutically unobjectionable placebo or a biogenous or synthetic gestagen, or a biogenous or synthetic estrogen, or a combination of two components, namely a biogenous estrogen, a synthetic estrogen and a gestagen or a combination of synthetic estrogen and a gestagen.

The description of the above document makes it clear that in the stage concept described therein there is typically a change of state over the period of time. Such a state change can take place in that the composition of the phases forming the stage is modified with respect to the components used and in that only the concentrations of the components used in the phases forming the stage undergo changes.

The problem of the invention is to provide a hormonal contraceptive product, which ensures high contraceptive safety or reliability and prevents inter-menstrual bleeding. There is also to be a further reduction in the side effects otherwise observed in hormonal contraceptive products.

According to the invention this problem is solved by a hormonal contraceptive product having two hormonal components, the agent comprising for continuous, combined administration a first hormonal component comprising at least one gestagen and a second hormonal component comprising at least one estrogen.

The problem is also solved by a hormonal contraception process, in which an a product, which comprises at least one first hormonal component, which comprises at least one gestagen, and a second hormonal component comprising at least one estrogen is continuously administered.

According to another aspect of the invention the product according to the invention is used for inhibiting ovulation.

According to a further aspect of the invention the product according to the invention is used for the treatment and/or prophylaxis of breast tumours.

According to another embodiment the invention proposes that gestagen as the first hormonal component is chosen from the group comprising progesterone, chlormadinone acetate, norethisterone acetate, cyproterone acetate, desogestrel, levenorgestrel, other natural and/or synthetic gestagens, anti-gestagens and hormonal analogs with gestagen or antigestagen action, as well as hormonal compounds which rapidly split off at least one gestagen following taking.

In the product according to the invention, the estrogen as the second hormonal component can be selected from the group comprising synthetic estrogens, biogenous estrogens, antiestrogens and hormonal analogs with estrogen or antiestrogen action.

In a preferred embodiment the synthetic estrogen is selected from the group comprising ethinyl estradiol, mestranol and the like, as well as hormonal compounds rapidly splitting off at least one synthetic estrogen following taking.

In particularly preferred manner the synthetic estrogen is ethinyl estradiol.

In preferred embodiments the daily administered ethinyl estradiol quantity is 1 to 20 μg. In particularly preferred manner, the daily administered ethinyl estradiol quantity is 5 to 10 μg.

According to the invention the biogenous estrogen is selected from the group comprising estradiol, estriol, estrone, estrane, etc., as well as hormonal compounds rapidly splitting off at least one biogenous estrogen after taking.

According to an embodiment the estradiol comprises 17-α-estradiol and/or 17-β-estradiol.

According to another embodiment the daily administered biogenous estrogen quantity in the case of estradiol, particularly α and β-estradiol, is 0.1 to 2 mg and in the case of conjugate estrogens 0.05 to 0.5 mg.

In an embodiment the product according to the invention can be administered orally.

In an alternative embodiment the product according to the invention can be administered transdermally.

In a second alternative embodiment the product according to the invention can be administered intravaginally.

In a third alternative embodiment the product according to the invention can be in depot injection form.

In a fourth alternative embodiment the product according to the invention can be administered as a hormonal implant.

Finally, the daily units in each case comprising both hormonal components, are placed in spatially separated and individually removable manner in a packaging unit.

In an embodiment of the process according to the invention the first hormonal component can be administered in combination with the second hormonal component.

In another embodiment of the process according to the invention the product according to the invention is administered.

The invention is based on the surprising finding that as a result of the continuous, combined administration of a product comprising two hormonal components, namely a first hormonal component comprising at least one gestagen and a second hormonal component comprising at least one estrogen, a high contraceptive reliability can be achieved.

In accordance with modern opinion, estrogens are not understood to cover steroid molecules, which preferably evolve their action in that they in different ways exert a biological effect at different cell locations in different organs. Estrogens can act (1) on the cellular membrane, (2) intracellular, cytoplasmic proteins and (3) specific nuclear receptors. It has recently become known that besides the standard estrogen receptor type 1 there is a second estrogen receptor type 2, whose organ distribution is different from that of the estrogen receptor type 1.

Thus, the above definition also covers the compounds known as "designer hormones", which have the aforementioned characteristics.

Thus, biogenous estrogens are steroid molecules, which evolve an estrogen-like action on the membrane, cytoplasmic proteins and nuclear receptors for hydrophobic ring substances and consequently trigger biological effects corresponding to a hydrophobic steroid ring structure able to initiate an estrogen-like action in cells, organs and the complete organism.

The term biogenous estrogens also covers those estrogens which are produced by the human body and consequently include endogenic estrogens. The biogenous estrogens used in specific embodiments of the product according to the invention are typically those which are chemically synthesized. However, it is fundamentally also possible to use compounds isolated from an organism.

Biogenous estrogens also cover conjugate, biogenous estrogens such as e.g. estradiol valerate and estrone sulphate.

The term antiestrogens is here understood to mean hydrophobic ring structure substances and other substances able to specifically and selectively counteract the above-described estrogen action on cells, organs or the overall organism.

Continuous administration is here understood to mean an administration uninterrupted over the use period, in which there are no hormonal component taking-free intervals. This means that there is no interruption of the administration of the product by administering placebos in place of the hormonal product. Thus, over the administration period typically lasting several months to years there are no changes to the fundamental composition of the hormonal components. Instead over the entire administration period the hormonal components forming the hormonal product according to the invention are administered uninterrupted and unchanged with no modification to the concentration. However, it is conceivable for the concentration of estrogen, understood in the full breadth of the concept defined here, and gestagen, also understood in the full breadth of the term defined here, can be changed for older women compared with younger women. This can also take place in such a way that over the continuous administration period initially there is a start with a specific composition and this is then adapted over a period of weeks, months and years to the changed biological needs of the women through the administration of a subsequent product, but which also comprises a product according to the present invention.

As a result of the continuous administration of said hormonal components it is ensured that the natural hormonal processes taking place in the female organism do not interrupt the contraceptive security.

As a result of the estrogen component, respectively by specific action of hydrophobic ring substances with an estrogen-like action, there can be a suppression of gonadotropins. This is desirable. The resulting suppression of the ovarial function is compensated by an adequate substitution of estrogen action. This prevents the development of osteoporosis, the favourable vascular effects of estrogens are maintained and there is no unfavourable influence to the lipid metabolism. By interrupting the cycle-dependent instability in the hormone system, the premenstrual syndrome can be favourably influenced. In addition, the physiological equilibrium of the coagulation system is not disturbed, because the unstable equilibrium in which the coagulation system occurs is not activated and deactivated by the up and down of hormone fluctuations. Thus, the hormonal product according to the invention is particularly suitable for women aged more than 40, where the risk of circulatory disturbances is known to increase with increasing age. There is also a reduction in the thrombosis risk, which has of late acquired considerable significance in contraceptive therapy.

It has surprisingly also been found that on administering the product according to the invention there is a reliable continuous suppression of the menstrual cycle and menstruation in the case of a very low dosage. Without wishing to be bound by this explanation, the combination of the two indicated hormonal components and in particular the low estrogen dosage would appear to be suitable for eliminating the otherwise conventional side effects of ethinyl estradiol and to drop below the administrations of more than 15 $\mu$g of ethinyl estradiol otherwise considered typically necessary in prior art contraceptives.

The low dosage of the two hormonal components and in particular the estrogen component is made possible by the additive action of the two hormonal components, without there being any limitation to the action of the product according to the invention with respect to its contraceptive and ovulation-inhibition properties.

The ovulation inhibition and menstrual cycle suppression reliably ensured by the product according to the invention is of great significance for certain patients, such as e.g. for top sports women, dancers and business women, who wish to exclude any reduction in their physical, intellectual and emotional efficiency as a result of the menstrual cycle. As a result of the combined, continuous administration of the two hormonal components of the product according to the invention it is possible to administer the same either orally, transdermally, intravaginally, by depot injections or hormone implants. Here again the advantages observed for the particular administration forms are obtained.

Possible oral administration forms are all the forms known from the prior art such as e.g. tablets, dragees, pills or capsules, which are produced using conventional adjuvants and carrier substances.

In the transdermal administration of the product according to the invention the two hormonal components forming the product can e.g. be applied to a plaster or also can be applied by transdermal, therapeutic systems and are consequently supplied to the organism. For example an already prepared combination of the two hormonal components or the latter individually can be introduced into such a system, which is based on ionotherapy or diffusion or optionally a combination of these effects.

In the case of oral administration it has proved appropriate to place the daily units, which in case comprise a combination of the two hormonal components, in a spatially separated and individually removable manner in a packaging unit, so that it is easy to check whether the typically daily taken, oral administration form has in fact been taken. It is important to ensure that there are no taking-free days. Depot injections can be administered at 1 to 6 months or longer intervals. Hormonal implants contain both hormonal components and deliver the same over a period of preferably 3 to 6 months.

When using the product according to the invention it has surprisingly been found that the treatment and/or prophylaxis of breast tumours is possible. The latest breast cancer risk research has revealed that mutations, which can be hereditary or acquired, occur in certain risk genes. Modern cancer therapy assumes that a cancerogenic mutation is present on one of the two allels of a gene which is initially controlled by the other, healthy allel. If a further mutation occurs in a specific organ cell on the second allel, then uncontrolled, malignant growth can occur.

Mutations on the second allel particularly frequently occur in given phases of the cell cycle, namely in the G1 phase. Every four weeks the menstrual cycle drives the breast cell in a cell cycle, "opens" the genome for mutations, which are either repaired or apoptotically "removed". Under the conditions of the conventional combined or sequential contraception treatment a women can have 500 to 700 cycles over her life span, whereas under natural conditions a women has a maximum of 20 to 30 cycles. Thus, in an unusually frequently number of cell cycles over in each case 8 days a considerable mutation risk is introduced into the stimulated breast tissue. If the menstrual cycle is suppressed, as is possible with the product according to the invention, the breast cells are brought into a "rest phase" and it is scientifically ensured that in the rest phase less cancerogenic mutations are introduced into a tissue than in a stimulated tissue. This reduces by a multiple mutagenesis, i.e. the breast cancer risk.

The aforementioned use of the product according to the invention for the treatment and/or prophylaxis of breast cancers is in particular associated with special advantages if the users of the product are high-risk subjects, such as e.g. those with a high family breast cancer risk.

The quantity of administered gestagens and estrogens substantially corresponds to the quantity of comparable prior art products. The examples provide further information concerning the quantities to be administered daily of the different compounds forming the first and/or second hormonal components.

The invention is explained in greater detail hereinafter relative to examples revealing further features, advantages and embodiments of the present invention.

EXAMPLE 1

For contraceptive treatment use was made of a product which per daily unit in table form contained 5 µg of ethinyl estradiol and 2 mg of norethisterone acetate. It is noteworthy that norethisterone acetate can be used in a concentration range of 0.5 to 5 mg. The product was administered for 9 months and revealed a very good contraceptive reliability whilst completely suppressing the menstrual cycle with no side effects. Within the framework of the present investigation it was ensured that the test persons took the product daily, i.e. without any taking interval, over the entire aforementioned time period.

EXAMPLE 2

For contraceptive treatment use was made of a product which per daily unit in table form contains 0.5 mg of estriol and 2 mg of chlormadinone acetate. It is noteworthy that estriol can be used in a concentration range of 0.5 to 3 mg and chlormadinone acetate in a concentration range of 0.75 to 5 mg. The product was administered for 12 months without any taking interval. The mode of action corresponded to that of example 1.

EXAMPLE 3

For contraceptive treatment use was made of a product which in each daily unit in tablet form contained 0.5 mg of estradiol valerate and 2 mg of lynestrenol. It is noteworthy that estradiol valerate can be used in a concentration range of 0.5 to 5 mg and lynestrenol in a concentration range of 0.5 to 4.5 mg. The product was administered for 12 months without any taking interval. The mode of action corresponded to that of example 1.

EXAMPLE 4

For contraceptive treatment use was made of a product containing per daily unit in tablet form 7.5 µg of ethinyl estradiol and 75 ug of desogestrel. It is noteworthy that desogestrel can be used in a concentration range of 50 to 200 µg. The product was administered for 12 months without any taking interval. The mode of action corresponded to that of example 1.

EXAMPLE 5

For contraceptive treatment use was made of a product containing per daily unit in tablet form 20 mg of tamoxifen and 2 mg of lutenyl. It is noteworthy that tamoxifen can be used in a concentration range of 10 to 50 mg and lutenyl in a concentration range of 1 to 5 mg. This product is preferably suitable for contraception in women with a family breast cancer risk. The product was administered for 12 months without any taking interval and the mode of action corresponded to that of example 1.

EXAMPLE 6

For contraceptive treatment use was made of a product containing per daily unit in tablet form 50 mg of raloxifen and 2.5 mg of medroxyprogesterone acetate (MPA). It is noteworthy that raloxifen can be used in a concentration range of 30 to 100 mg and medroxyprogesterone acetate in a concentration range of 2 to 10 mg. This combination is preferably suitable for women with a family breast cancer risk and young women who have suffered breast cancer. The product was administered for 12 months without any taking interval and the mode of action corresponded to that of example 1.

EXAMPLE 7

For contraceptive treatment use was made of an agent containing per daily unit in tablet form 10 µg of ethinyl estradiol and tibolone in a daily concentration of 2 mg. It is noteworthy that tibolone can be used with a concentration of 1 to 10 mg. The product was administered without any taking interval for 12 months and the mode of action corresponded to that of example 1.

EXAMPLE 8

For contraceptive treatment use was made of a product containing per daily unit in tablet form 10 µg of ethinyl estradiol and as the antiestrogen substance Ro486 in a concentration of 2.5 mg. It is noteworthy that R0486 can be used in a concentration range of 1 to 7.5 mg. The product was administered without any taking interval over a period of 12 months and the mode of action corresponded to that of example 1.

The features of the invention described in the description and claims can be essential individually and in random combination for the implementation of the different embodiments of the invention.

What is claimed is:

1. A method for hormonal contraception, comprising:
    administering orally, transdermally or via depot to a mammal in need thereof, for a continuous and uninterrupted administration period of greater than 110 days, a contraceptive product comprising:
        a gestagen selected from the group consisting of progesterone, chlormadinone acetate, norethisterone acetate, cyprotherone acetate, desogestrel, and levonorgestrel; and
        an estrogen selected from the group consisting of ethinyl estradiol, mestranol, estradiol, estriol, estrone, and estrane;
    wherein said gestagen and said estrogen are present in said contraceptive product at unchanged dosages throughout the administration period, and when said estrogen is ethinyl estradiol, the dosage of ethinyl estradiol is not greater than 20 µg per day.

2. The method of hormonal contraception of claim 1 wherein the dosage of ethinyl estradiol is between 1 and 20 µg per day.

3. A method for continuous suppression of the menstrual cycle, comprising:
    administering orally, transdermally or via depot to a mammal in need thereof, for a continuous and uninterrupted administration period of greater than 110 days, a contraceptive product comprising:
        a gestagen selected from the group consisting of progesterone, chlormadinone acetate, northisterone acetate, cyprotherone acetate, desogestrel, and levonorgestrel; and
        an estrogen selected from the group consisting of ethinyl estradiol, mestranol, estradiol, estriol, estrone, and estrane;
    wherein said gestagen and said estrogen are present in said contraceptive product at unchanged dosages throughout the administration period, and wherein the dosage of ethinyl estradiol is not greater than 20 µg per day, such that the menstrual cycle is continuously suppressed throughout the administration period.

* * * * *